United States Patent [19]

Cobb et al.

[11] Patent Number: 4,777,305
[45] Date of Patent: Oct. 11, 1988

[54] SYNTHESIS OF 1,4-DICHLOROBENZENE

[75] Inventors: Raymond L. Cobb, Maretta, Ohio; Michael D. Mitchell, Bartlesville, Okla.

[73] Assignee: Phillips Petroleum Company, Bartlesville, Okla.

[21] Appl. No.: 111,964

[22] Filed: Oct. 22, 1987

[51] Int. Cl.$^4$ ............................................. C07C 17/12
[52] U.S. Cl. ................................. 570/208; 570/206; 570/207
[58] Field of Search ........................ 570/206, 207, 208

[56] References Cited

U.S. PATENT DOCUMENTS

| 3,216,789 | 11/1965 | Breck et al. | 23/113 |
| 4,645,588 | 2/1987 | Buss et al. | 208/138 |

FOREIGN PATENT DOCUMENTS

| 0118851 | 9/1984 | European Pat. Off. | 570/208 |
| 0154236 | 9/1985 | European Pat. Off. | 570/208 |
| 0195514 | 9/1986 | European Pat. Off. | 570/208 |
| 0225723 | 6/1987 | European Pat. Off. | 570/208 |

OTHER PUBLICATIONS

"Properties of Ammonium Exchanged Type L Zeolite", by Y. Ono et al., Chem. Soc. Faraday Transactions I, 72, 1976, pp. 2150–2160.

"Acidity, Catalytic Activity and Thermal Stability of Various L Zeolites", by C. Parra et al., Journal of Catalysis, 40, pp. 52–60.

*Primary Examiner*—Werren B. Lone
*Attorney, Agent, or Firm*—K. K. Brandes

[57] ABSTRACT

In a process for reacting an aromatic compound (preferably chlorobenzene) with free chlorine in the presence of a catalyst comprising a zeolite of the L family (zeolite L) under such reaction conditions as to obtain a product comprising 1,4-dichlorobenzene, the improvement comprises employing ammonium ion-exchanged zeolite of the L family.

17 Claims, No Drawings

SYNTHESIS OF 1,4-DICHLOROBENZENE

BACKGROUND OF THE INVENTION

In one aspect, this invention relates to a process for chlorinating benzene and/or chlorobenzene so as to produce 1,4-dichlorobenzene at high selectivity. In another aspect, this invention relates to the use of zeolite catalysts for chlorinating benzene and/or monochlorobenzene.

It is known to produce 1,4-dichlorobenzene by direct chlorination of benzene or chlorobenzene in the presence of a zeolite of the L family as catalyst. However, there is an ever present need to develop new processes or producing 1,4-dichlorobenzene at a higher selectivity by employing more effective catalysts than those presently known.

SUMMARY OF THE INVENTION

It is an object of this invention to react benzene and/or chlorobenzene with chlorine so as to produce 1,4-dichlorobenzene at high selectivity. It is a further object of this invention to use ion-exchanged zeolites of the L family as catalysts in the above-identified reactions for enhanced selectivity to 1,4-dichlorobenzene. Other objects and advantages will be apparent from the detailed description and the appended claims.

In accordance with this invention, an aromatic feed comprising at least one aromatic compound selected from the group consisting of benzene and chlorobenzene is contacted with free chlorine and a catalyst composition comprising an ammonium ion-exchanged zeolite of the L family, under such reaction conditions as to obtain a product stream comprising 1,4-dichlorobenzene. Optionally, said ammonium ion-exchanged zeolite is additionally ion-exchanged with transition metal. The presently preferred aromatic feed consists essentially of chlorobenzene.

DETAILED DESCRIPTION OF THE INVENTION

Any aromatic feed which contains benzene or chlorobenzene or a mixture of both can be used in the chlorination process of this invention. The aromatic feed may contain suitable diluents, such as liquid paraffins and the like. The feed preferably consists essentially of benzene, chlorobenzene or a mixture thereof. Most preferably undiluted liquid chlorobenzene is used as the aromatic feed. The aromatic feed can be contacted with free chlorine and the catalyst composition, in accordance with the chlorination process of this invention, in any suitable manner. Free chlorine can be added as gaseous chlorine or liquid chlorine, optionally diluted with inert diluent. The aromatic feed and free chlorine can be premixed, or they can be charged separately in any order to a reactor and then substantially mixed in the reactor.

The catalyst composition, which is selective for producing 1,4-dichlorobenzene when employed in the chlorination process of this invention, comprises a zeolite of the L family (also referred to as zeolite L) which has been ion-exchanged with an ammonium ion (preferably $NH_4^+$) and optionally also with at least one ion of at least one suitable transition metal (i.e., a metal belonging to Group IIIB-VIIB, VIII, IB and IIB of the Periodic Table, as defined by Webster's New Collegiate Dictionary, 1977, page 852). Any suitable zeolite of the L family can be used for ion-exchange with an ammonium ion (and optionally also with the transition metal ion). The term "zeolite of the L family" is defined in U.S. Pat. No. 4,645,588, the disclosure of which is herein incorporated by reference. Additional information on zeolites of the L family (zeolite L) are provided in U.S. Pat. No. 3,216,789, the disclosure of which is herein incorporated by reference. The presently preferred zeolite of the L family (before ion-exchange with ammonium) is in the potassium form, hereinafter referred to as zeolite L-K. Zeolite L-K is commercially available as "Linde SK45", now designated "Molecular Sieve ELZ-L", from Union Carbide Corporation, Danbury, Ct.

The ion-exchanging of the zeolite of the L family, preferably zeolite L-K, can be carried out in any suitable manner. Generally, the zeolite is contacted with an ion-exchange solution of an ammonium compound dissolved in any suitable solvent (preferably water) under any suitable contacting conditions. Non-limiting examples of suitable inorganic and organic ammonium compounds are: $NH_4F$, $NH_4Cl$, $NH_4Br$, $NH_4I$, $NH_4NO_3$, $NH_4HSO_4$, $(NH_4)_2SO_4$, methylammonium chloride, dimethylammonium chloride, octylammonium chloride, dodecylammonium chloride, cetylammonium chloride, and the like; preferably $NH_4$ compounds, more preferably $NH_4Cl$.

When the zeolite of the L family is ion-exchanged with an ammonium ion and at least one transition metal ion, preferably $Ni^{+2}$, $Co^{+2}$ or at least one lanthanide ion (in particular $Sm^{+3}$ and/or $La^{+3}$), said ion-exchange solution preferably contains both at least one ammonium compound and at least one transition metal compound, which are at least partially soluble in the solvent, preferably water. Presently preferred transition metal compounds are chlorides of Ni, Co and lanthanide metals (in particular Sm and/or La). It is within the scope of this invention to carry out sequential ion-exchange (i.e., exchange with ammonium ion first, then exchange with transition metal ion; or vice versa). However, these sequential ion-exchange methods are presently not preferred.

Any suitable concentration of the ammonium compound and of at least one compound of at least one transition metal (when used) in the ion-exchange solution can be employed. Generally, the concentration of the ammonium compound is in the range of from about 0.2 to about 3.0 mole/l (preferably about 0.5–2.0 mol/l); and the concentration of the transition metal compound (when used) is in the range of from about 0.1 to about 0.6 mole/l. If at least one transition metal is used in addition to the ammonium compound, the weight ratio of ammonium compound to said at least one transition metal compound is generally in the range of from about 1:2 to about 20:1, preferably from about 1:1 to about 10:1.

Any suitable ratio of the zeolite of the L family to dissolved ammonium compound can be employed in the ion-exchange step. Generally, the weight ratio of the zeolite of the L family to the dissolved ammonium compound is in the range of from about 1:5 to about 10:1, preferably from about 1:2 to about 5:1. Any suitable temperature conditions can be employed in the ion-exchange procedure. Generally, the temperature is in the range of from about 40° to about 90° C., preferably from about 50° to about 80° C. Any suitable pressure conditions can be employed during ion-exchanging of the zeolite, preferably about atmospheric (about 1 atm.).

Any suitable time period for the contact of the zeolite and the ion-exchange solution can be selected, generally from about 10 to about 200 minutes, preferably from about 10 to about 60 minutes.

The preferred method of contacting of the zeolite of the L family with the ion-exchange solution is mixing (i.e., impregnating the zeolite with the ion-exchange solution). After the ion-exchange is complete, the ion-exchanged zeolite material is preferably separated from the ion-exchange solution, and washed with a suitable liquid (generally water). The ion-exchanged zeolite is heated so as to substantially dry the ion-exchanged zeolite (preferably at about 80°–150° C., for about 10 minutes to about 20 hours, preferably under vacuum conditions).

The chlorination process of this invention can be carried out as a batch process or as a continuous process, the latter being preferred. In a continuous operation, an aromatic feed stream and a free chlorine containing feed stream are generally metered separately and are continuously charged to a reaction zone in the form of a reactor, which contains the catalyst as a fixed bed. These two feed streams are then mixed by mechanical stirring or by static mixing means before they flow through the fixed catalyst bed in any direction (upflow, downflow or horizontal), under suitable reaction conditions. A fluidized catalyst bed operation is also possible, but is presently not preferred. The term "stream", whenever used in this application, applies to both continuous and batch operations.

Any suitable reaction conditions for the chlorination process can be employed. The weight ratio of the aromatic feed compound (benzene or chlorobenzene or both) to free chlorine can range from about 1:20 to about 200:1, and is preferably in the range of from about 1:1 to about 10:1. When the preferred feed compound, chlorobenzene, is employed, the range of the weight ratio of chlorobenzene to chlorine more preferably is about 1:1 to about 3:1. The weight ratio of the aromatic feed compound to the catalyst composition can range from about 1:1 to about 100:1, and preferably is in the range of from about 2:1 to about 20:1.

Any suitable reaction temperature can be employed in the chlorination process of this invention. Generally, the reaction temperature is in the range of from about 20° C. to about 200° C., preferably from about 60° C. to about 130° C. The reaction pressure can be subatmospheric, atmospheric (preferred) or superatmospheric. Any suitable reaction time, i.e., the time of intimate contact between aromatic feed stream, free chlorine containing stream and the catalyst composition can be employed. The reaction time can range from about 1 second to about 50 hours, depending on the temperature, the degree of agitation and the specific catalyst composition used, and will preferably be in the range of from about 0.5 minute to about 2 hours (more preferably about 10–60 minutes).

Any formed product, primarily p-dichlorobenzene, can be separated (and recovered) from the product stream comprising unreacted aromatic feed compound(s), unreacted hhlorine and other formed products in any suitable manner, preferably by fractional distillation. Unreacted aromatic feed and chlorine can be recycled to the chlorination reactor. The desired product, para-dichlorobenzene, is useful as a reactant in the process for preparing poly(phenylene sulfide).

The following examples are presented for further illustration of the invention and are not to be considered as unduly limiting the scope of this invention.

EXAMPLE I

This example illustrates various zeolite L-K catalysts which were employed in the chlorination process of this example.

Catalyst A (Control) was a K-type zeolite of the L family, provided by Union Carbide Corporation under the product designation of Molecular Sieve ELZ-L. Pertinent physical and structural parameters of ELZ-L were as follows. Approximate empirical formula: $K_2O\cdot Al_2O_3 0.5H_2O$; $Al_2O_3$ content (on anhydrous basis): 18.1 weight-%; $SiO_2$ content (on anhydrous basis): 64.9 weight-%; $K_2O$ content (on anhydrous basis): 15.3 weight-%; $BET/N_2$ surface area: 386 $m^2/g$; crystal density: 2.1 g/cc; unit cell constants $a_o=18.4A$ and $c_o=7.5A$; absorption of $O_2$: 15.5 weight-%; provided in powder form; stable in air up to 850° C.

Catalyst B (Control) was prepared by heating Catalyst A with water at about 60°–70° C. Catalyst B was recovered by filtration and dried in vacuum at about 110° C. for about 16 hours.

Catalyst C (Invention) was prepared by mixing 10–15 cc of Catalyst A with about 100 cc of an aqueous solution which contained about 10/grams of $NH_4Cl$. The obtained slurry was stirred at 60°–70° C. for about 15–20 minutes and filtered. The filter cake was washed with deionized water and then dried (as described for Catalyst B). Catalyst C* was dried in a Rotovap drier without prior filtering.

Catalyst D (Invention) was prepared essentially in accordance with the procedure for Catalyst C, except that the ion-exchange with the $NH_4Cl$ solution was carried out twice, with subsequent filtration, washing and drying (as described above).

Catalyst E (Invention) was prepared essentially in accordance with the procedure for Catalyst B, except that the ion-exchange with the $NH_4Cl$ solution procedure was carried out three times, with subsequent filtaation, washing and drying (as described above).

Catalyst F (Control) was prepared by calcining Catalyst C at 400° C. in air for about 16 hours (so as to drive out $NH_3$).

Catalyst G (Invention) was prepared in accordance with the procedure for Catalyst C, except that the aqueous solution contained about 2 grams of $NiCl_2$ in addition to about 10 grams of $NH_4Cl$.

Catalyst H (Invention) was prepared in accordance with the procedure for Catalyst C, except that the aqueous solution contained about 2 grams of $CoCl_2$ in addition to about 10 grams of $NH_4Cl$.

Catalyst I (Invention) was prepared in accordance with Catalyst C, except that the aqueous solution contained about 2 grams of $SmCl_3$ in addition to about 10 grams of $NH_4Cl$.

Catalyst K (Invention) was prepared in accordance with the procedure for Catalyst C, except that the aqueous solution contained about 2 grams of $NiCl_2$ and 2 grams of $SmCl_3$ in addition to about 10 grams of $NH_4Cl$).

Catalyst L (Invention) was prepared in accordance with the procedure for Catalyst C, except that the aqueous solution contained about 2 grams of $NiCl_2$ and about 2 grams of mixed rare earth chlorides (mixed lanthanide chlorides, including $LaCl_3$) in addition to about 10 grams of $NH_4Cl$.

EXAMPLE II

This example illustrates the conversion of chlorobenzene to dichlorobenzenes, primarily 1,4-dichlorobenzene (p-DCB), in the presence of the zeolite L catalysts of Example I, in accordance with the process of this invention.

About 50 cc chlorobenzene and about 5 cc of one of the zeolite catalysts described in Example I were added to a glass reactor. This mixture was stirred and heated to a temperature ranging from about 25° C. to about 120° C., depending on the catalyst system used, while chlorine gas was introduced during a time period of about 30 minutes at a rate of about 1 cc per minute.

The reaction product was cooled and analyzed by gas-liquid chromatography employing a Hewlett-Packard HP5880 instrument equipped with a flame ionization detector and a capillary absorption column (length: 50 m) the inside wall of which was coated with cross-linked methylsilicone. The column was held at 50° C. for 8 minutes, and then heated at a rate of 10° C./minute to 250° C. Typical retention times under these conditions were: 9.50 minutes for chlorobenzene (Cb), 14.70 minutes for meta-dichlorobenzene (m-DCB), 14.90 minutes for p-DCB, 15.60 minutes for ortho-dichlorobenzene (o-DCB), and 19.0+ minutes for tri- and tetra-chlorobenzenes. Test results are summarized in Table I.

TABLE I

| Run | Catalyst | Temp. (°C.) | Conversion of CB (%) | Ratio of p-DCB/o-DCB |
|---|---|---|---|---|
| 1 (Control) | A | 75–80 | 12 | 6.5 |
| 2 (Control) | A | 90–95 | 28 | 6.8 |
| 3 (Control) | B | 80–95 | 36 | 8.0 |
| 4 (Invention) | C | 70–80 | 28 | 9.5 |
| 5 (Invention) | C | 80–85 | 20 | 6.8 |
| 6 (Invention) | C | 90–95 | 57 | 7.9 |
| 7 (Invention) | C | 90–100 | 67 | 8.0 |
| 8 (Invention) | C* | 80–90 | 29 | 12.6 |
| 9 (Invention) | C* | 90–95 | 15 | 10.5 |
| 10 (Invention) | D | 80–85 | 14 | 8.4 |
| 11 (Invention) | D | 90–95 | 38 | 7.7 |
| 12 (Invention) | D | 100–105 | 78 | 8.0 |
| 13 (Invention) | D | 115–120 | 69 | 5.8 |
| 14 (Invention) | E | 70–75 | 8[1] | 10.1 |
| 15 (Invention) | E | 70–80 | 41 | 11.3 |
| 16 (Invention) | E | 100–105 | 84 | 7.3 |
| 17 (Invention) | E | 100–105 | 70 | 8.1 |
| 18 (Control) | F | 95–100 | 30 | 2.8 |
| 19 (Invention) | G | 90–95 | 77 | 9.6 |
| 20 (Invention) | G | 90–100 | 66 | 8.1 |
| 21 (Invention) | G | 95–100 | 33 | 8.1 |
| 22 (Invention) | G | 110–115 | 52 | 7.2 |
| 23 (Invention) | G | 110–115 | 70 | 6.4 |
| 24 (Invention) | H | 75–80 | 35 | 8.6 |
| 25 (Invention) | H | 100–105 | 53 | 7.8 |
| 26 (Invention) | H | 115–120 | 67 | 6.3 |
| 27 (Invention) | I | 85–95 | 48 | 8.8 |
| 28 (Invention) | I | 95–100 | 61 | 8.9 |
| 29 (Invention) | K | 80–85 | 34 | 8.1 |
| 30 (Invention) | K | 95–100 | 45 | 8.3 |
| 31 (Invention) | L | 75–80 | 33 | 7.3 |
| 32 (Invention) | L | 95–100 | 33 | 7.3 |

[1]result believed to be erroneous.
Note:
A test run with Catalyst C at 25–30° C. resulted in a CB conversion of 12% and a p-DCB/o-DCB ratio of 10.8.

Test results in Table I show that generally the conversion of chlorobenzene and the ratio of para-DCB to ortho-DCB (a measure of selectivity to para-DCB) were higher for the $NH_4^+$-ion exchanged zeolite L-K catalysts, especially those having repeatedly been ion-exchange with $NH_4^+$ (see runs with Catalysts D and E), than for the untreated zeolite L-K (Catalyst A) or the water-treated zeolite L-K (Catalyst B). When the $NH_4^+$-ion exchanged zeolite L-K was calcined at 400° C., it apparently lost $NH_3$, and a much lower ratio of para-DCB to ortho-DCB was attained (see Run with Catalyst F). Thus the ammonium-exchanged catalyst must not be calcined or otherwise heated above about 200° C. after the ion-exchange. The zeolite L-K catalysts that had been ion-exchanged with $NH_4^+$ and also at least one transition metal (Catalysts G, H, I, K and L) did not perform better (in terms of conversion and p-DCB/o-DCB ratio) than zeolite L-K catalysts that had been ion-exchanged only with $NH_4^+$ (Catalysts C, D and E).

Reasonable variations, modifications and adaptations for various usages and conditions can be made within the scope of the disclosure and appended claims, without departing from the scope of this invention.

That which is claimed is:

1. A process for producing 1,4-dichlorobenzene which comprises the step of contacting an aromatic feed comprising at least one aromatic feed compound selected from the group consisting of benzene and chlorobenzene with free chlorine and a catalyst composition comprising an ammonium ion-exchanged zeolite of the L family, under reaction conditions in a reaction zone and obtaining a product comprising 1,4-dichlorobenzene.

2. A process in accordance with claim 1 wherein said aromatic feed compound is chlorobenzene and wherein said ammonium ion-exchanged zeolite of the L family has been prepared by ion-exchanging zeolite of the L family with a solution comprising at least one dissolved $NH_4$ compound.

3. A process in accordance with claim 2 wherein said ammonium ion-exchanged zeolite of the L family has been prepared by ion-exchanging zeolite of the L family with a solution comprising dissolved $NH_4Cl$.

4. A process in accordance with claim 2 wherein the concentration of said dissolved $NH_4$ compound in said solution is in the range of from about 0.2 to about 3.0 mole/l.

5. A process in accordance with claim 2 wherein said ion-exchanging is carried out at a weight ratio of said zeolite of the L family to said dissolved $NH_4$ compound in the range of from about 1:5 to about 10:1.

6. A process in accordance with claim 5 wherein said ion-exchanging is carried out at a temperature of about 40°–90° C. for about 10–200 minutes.

7. A process in accordance with claim 2 wherein said solution additionally comprises at least one compound of at least one transition metal.

8. A process in accordance with claim 7 wherein said at least one transition metal is selected from the group consisting of cobalt, nickel and lanthanides.

9. A process in accordance with claim 7 wherein the weight ratio of said $NH_4$ compound to said at least one compound of at least one transition metal is in the range of from about 1:2 to about 20:1.

10. A process in accordance with claim 1 wherein said aromatic feed compound is chlorobenzene and said reaction conditions comprise a weight ratio of chlorobenzene to free chlorine in the range of from about 1:20 to about 200:1, and a weight ratio of chlorobenzene to said catalyst composition is in the range of from about 1:1 to about 100:1.

11. A process in accordance with claim 10 wherein said weight ratio of chlorobenzene to free chlorine is in the range of from 1:1 to about 10:1, and said weight ratio of chlorobenzene to said catalyst composition is in the range of from about 2:1 to about 20:1.

12. A process in accordance with claim 10 wherein said reaction conditions further comprise a reaction temperature in the range of from about 20 to about 200° C. and a reaction time of from about 1 second to about 50 hours.

13. A process in accordance with claim 1 comprising the additional step of separating 1,4-dichlorobenzene from said product.

14. A process in accordance with claim 13 wherein unreacted aromatic feed compound and unreacted chlorine are recycled to said reaction zone.

15. A process in accordance with claim 1 wherein said feed consists essentially of benzene, chlorobenzene or a mixture thereof.

16. A process in accordance with claim 1 wherein said process is carried out in a continuous manner by premixing a stream of said aromatic feed and a stream of said free chlorine and passing said thus mixed stream through said reaction zone wherein said catalyst composition in the form of a fixed bed.

17. A process in accordance with claim 10 wherein said process is carried out in a continuous manner by premixing a stream of said aromatic feed and a stream of said free chlorine and passing said thus mixed stream through said reaction zone wherein said catalyst composition in the form of a fixed bed.

* * * * *